United States Patent [19]

Isogai et al.

[11] 4,327,225
[45] Apr. 27, 1982

[54] PROCESS FOR PRODUCING 2-PENTENOIC ESTER

[75] Inventors: Nobuo Isogai; Motoyuki Hosokawa; Takashi Okawa; Natsuko Wakui, all of Niigata, Japan

[73] Assignee: Mitsubishi Gas Chemical Co., Inc., Tokyo, Japan

[21] Appl. No.: 195,524

[22] Filed: Oct. 9, 1980

[30] Foreign Application Priority Data

Oct. 12, 1979 [JP] Japan ................................ 54/131377

[51] Int. Cl.$^3$ ............................................ C07C 67/333
[52] U.S. Cl. ..................................... 560/205; 252/426
[58] Field of Search .......................... 560/205; 252/426

[56] References Cited

PUBLICATIONS

Sakai, Mutsuji et al., *Bull. Chem. Soc. Japan*, vol. 51, (1978) 2970–2972.
Bergson, Goran et al., *Chemical Abstracts*, vol. 88, #189,890w.
Rhoads, Sara Jane et al., *J. Org. Chem.*, vol. 35 (1970) pp. 3352–3358.

*Primary Examiner*—Natalie Trousof
*Assistant Examiner*—L. Hendriksen
*Attorney, Agent, or Firm*—Frishauf, Holtz, Goodman & Woodward

[57] ABSTRACT

A process for producing a 2-pentenoic ester which comprises isomerizing the corresponding 3-pentenoic ester in the presence of a dicyclized amidine is disclosed.

5 Claims, No Drawings

PROCESS FOR PRODUCING 2-PENTENOIC ESTER

BACKGROUND OF THE INVENTION

This invention relates to a process for producing a 2-pentenoic ester which comprises isomerizing the corresponding 3-pentenoic ester.

In general, many prior processes for isomerizing unsaturated carboxylates are known. For example, (a) J. Chem. Soc. 2454 (1957) discloses a process for isomerizing a 3-hexenoic ester in the presence of potassium hydroxide as a catalyst; (b) J. Org. Chem. 35 3352 (1970) discloses a process for isomerizing methyl 3-pentenoic ester in the presence of sodium methylate or iron pentacarbonyl; and (c) Bull. Chem. Soc. Jpn., 51 2970 (1978) discloses a process for isomerizing dimethyl methylenesuccinate to dimethyl 2-methylbutenoate by using triethylamine.

However, in process (a), the ester employed as a starting material is hydrolyzed by the alkali hydroxide to form the alkali salt of unsaturated carboxylic acid. In order to avoid this shortcoming, the unsaturated carboxylate which is a starting material should be neutrilized, isomerized and esterified. This is complicated.

In process (b) in which sodium methylate is used, sodium methylate adds to the double bond of the unsaturated carboxylate. This lowers the yield of 2-pentenoic ester. In process (b) in which iron pentacarbonyl is used, the reaction speed is slow and, also, the reaction is necessarily effected under an atmosphere pressurized by carbon monoxide, because iron pentacarbonyl is unstable.

In process (c), isomerization of dimethyl methylenesuccinate to dimethyl 2-methylbutenoate proceeds in the presence of triethylamine even at room temperature, and little side reaction occurs. However, isomerization reaction of a 3-pentenoic ester to the corresponding 2-pentenoic ester in the presence of triethylamine alowly proceeds at 100° C. This is too slow to be industrially practicable.

SUMMARY OF THE INVENTION

The inventors of this invention found that a 3-pentenoic ester, particularly an alkyl ester of 3-pentenoic acid is isomerized to the corresponding 2-pentenoic ester in the presence of a dicyclized amidine in a high yield at excellent reaction speed and without substantially occuring side reaction.

An object of this invention is to provide a process for producing a 2-pentenoic ester from the corresponding 3-pentenoic ester in a high yield at fast reaction speed and without occuring undesirable side reaction substantially.

This invention relates to a process for producing a 2-pentenoic ester which comprises isomerizing the corresponding 3-pentenoic ester in the presence of at least one dicyclized amidine.

DETAILED DESCRIPTION OF THE INVENTION

The dicyclized amidines employed in the practice of this invention include for example 1,8-diazabicyclo(5,4,0)-undesene-7 (hereinafter referred to as DBU) represented by the formula

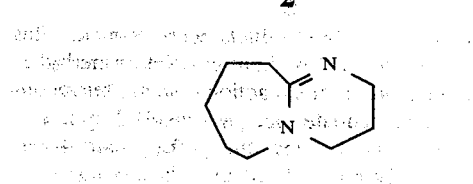

and 1,5-diazabicyclo(4,3,0)nonene-5 (hereinafter referred to as DBN) represented by the formula

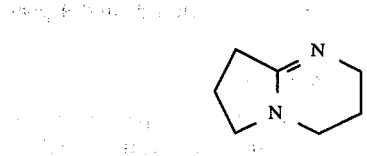

mixture of the dicyclized amidines.

The dicyclized amidine does not change during the isomerization reaction; it merely accelerates the reaction and can easily be separated from the reaction system through distillation for reuse.

The amount of dicyclized amidine employed is not critical. In general, dicyclized amidine in an amount 0.01-2.0 moles, preferably 0.01-1.0 mole may be used per 1 mole of the 3-pentenoic ester. Though the isomerization reaction will proceed in the presence of a dicyclized amidine in amount of even less than 0.01 mole per 1 mole of 3-pentenoate, but the reaction proceeds slowly. The use of a dicyclized amidine in an amount of more than 2.0 moles per 1 mole of 3-pentenoic ester does not interfere with the reaction, but the use of more than this merely adds to production cost.

The isomerization reaction temperature is not critical. The temperature may range from room temperature to 200° C., preferably 30°–150° C. Though the reaction proceeds at a temperature below room temperature, this is not preferable because of the slower reaction speed. On the other hand, a temperature higher than 200° C. is likely to cause side reactions.

The reaction pressure may be effected under reduced pressure, atmospheric pressure or superpressure.

The isomerization reaction may be effected without any solvent or in the presence of at least one solvent. The solvents employed in the practice of this invention include aliphatic or aromatic hydrocarbons, ethers, amides, nitriles, ketones, tertiary amines, esters of organic acids, dialkyl sulfoxides and sulforane. Particularly, when dialkyl sulfoxides, such as dimethyl sulfoxide, sulforane and N-alkyl phosphoric triamide, such as hexamethyl phosphoric triamide are used as a solvent at relatively low temperature, yield of reaction increases. The solvent is conveniently used in order to circulate dicyclized amidine for reuse. A solvent in amount of 0–20 moles may be used per 1 mole of 3-pentenoic ester. More solvent than this can be used, but this is not economical.

This invention is further illustrated by the following non-limiting Examples.

EXAMPLE 1

Into a 100 ml triangle flask were charged 20 grs. of methyl 3-pentenoate and 20 grs. of DBU. The isomerization reaction was effected for one hour with stirring by magnet stirrer while maintaining the flask in oil bath of 100° C. The resulting reaction mixture contained 0.86 grs. of methyl 4-pentenoate, 6.99 grs. of methyl 3-pentenoate and 12.12 grs. of methyl 2-pentenoate. This shows that yield of methyl 2-pentenoate is 60.6 mole %.

Substantial no other by-products were formed. This yield is the one obtained without circulating methyl 3- and 4-pentenoate left in the reaction system after recovering methyl 2-pentenoate (one pase yield). In practice, the yield becomes better, since the methyl 3- and 4-pentenoate are usually recirculated into the isomerization zone for further isomerization reaction. The yields given in the following examples are all the ones obtained without recirculating the methyl 3- and 4-pentenoate.

EXAMPLE 2

The procedure of Example 1 was repeated except that 2 grs. of DBU was used. The reaction mixture contained 0.98 grs. of methyl 4-pentenoate, 7.58 grs. of methyl 3-pentenoate and 11.44 grs. of methyl 2-pentenoate. The yield of methyl 2-pentenoate was 57.7 mole %. Substantially no other by-products are formed.

EXAMPLE 3

The procedure of Example 1 was repeated except that the reaction temperature was 30° C. The reaction mixture contained 0.62 grs. of methyl 4-pentenoate, 10.90 grs. of methyl 3-pentenoate and 8.48 grs. of methyl 2-pentenoate. Therefore, the yield of methyl 2-pentenoate was 42.4 mole %. Substantially no other by-products were formed.

EXAMPLE 4

The procedure of Example 1 was repeated except that ethyl 3-pentenoate was used in place of methyl 3-pentenoate. The reaction mixture contained 0.58 grs. of ethyl 4-pentenoate, 7.64 grs. of ethyl 3-pentenoate and 11.76 grs. of ethyl 2-pentenoate. The yield of ethyl 2-pentenoate was 58.8 mole %. Substantial no other by-products were formed.

EXAMPLE 5

Into a 100 ml triangle flask were charged 2 grs. of methyl 3-pentenoate, 2 grs. of DBU and 15 ml of dimethyl sulfoxide. The isomerization reaction was effected for one hour with stirring by magnet stirrer while maintaining the flask in an oil bath of 30° C.

The reaction mixture contained 0.06 grs. of methyl 4-pentenoate, 0.99 grs. of methyl 3-pentenoate and 0.95 grs. of methyl 2-pentenoate. The yield of methyl 2-pentenoate was 47.5 mole %. Substantial no other by-products were formed.

EXAMPLE 6

The procedure of Example 5 was repeated except that sulforane was used in place of dimethyl sulfoxide. The reaction mixture contained 0.08 grs. of methyl 4-pentenoate, 0.94 grs. of methyl 3-pentenoate and 0.98 grs. of methyl 2-pentenoate. The yield of methyl 2-pentenoate was 49.0 mole %. Substantial no other by-products were formed.

EXAMPLE 7

The procedure of Example 5 was repeated except that 15 ml of hexamethyl phosphoric triamide was used in place of dimethyl sulfoxide. The reaction mixture contained 0.07 grs. of methyl 4-pentenoate, 1.00 gr. of methyl 3-pentenoate and 0.92 grs. of methyl 2-pentenoate. The yield of methyl 2-pentenoate was 46.0 mole %. Substantial no other by-products were formed.

EXAMPLE 8 AND CONTROL TESTS 1–2

Into a 100 ml triangle flask were charged 2 grs. of methyl 3-pentenoate, 15 ml of dimethyl sulfoxide and 2 grs. of DBU (in Example 8). The isomerization reaction was effected with stirring by magnet stirrer for reaction times as given in Table 1 while maintaining the flask in oil bath of 100° C.

For comparison, the above procedures were repeated except each of triethylamine (in Control 1) and iron pentacarbonyl (in Control 2) was used in place of DBU. The results are shown in Table 1.

TABLE 1

| Reaction time (hr.) | Yield of methyl 2-pentenoate (mole %) | | |
|---|---|---|---|
| | Example 8 | Control test 1 | Control test 2 |
| 0.5 | 59 | — | — |
| 1 | 60 | 15 | 6 |
| 3 | 61 | 28 | 16 |
| 5 | — | 34 | 22 |
| 10 | — | 43 | 32 |
| 15 | — | 48 | 37 |

What is claimed is:

1. A process for producing a 2-pentenoic ester which comprises isomerizing the corresponding 3-pentenoic ester in the presence of dicyclized amidine selected from the group consisting of 1,8-diazabicyclo(5,4,0)undecene-7, represented by the formula

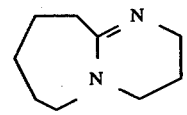

and 1,5-diazabicyclo(4,3,0)nonene-5 represented by the formula

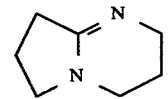

and mixtures thereof.

2. The process as defined in claim 1 wherein amount of the dicyclized amidine is in the range of 0.01 mole to 2.0 mole per 1 mole of 3-pentenoate.

3. The process as defined in claim 1 or 2 wherein the isomerization is effected at a temperature between room temperature and 200° C.

4. The process as defined in claim 1 or 2 wherein the isomerization is effected in the presence of solvent selected from the group consisting of aliphatic or aromatic hydrocarbons, ethers, amides, nitriles, ketones, tertiary amines, esters of organic acids, dialkyl sulphoxides, sulforane and mixtures thereof.

5. The process as defined in claim 3 wherein the isomerization is effected in the presence of solvent selected from the group consisting of aliphatic or aromatic hydrocarbons, ethers, amides, nitriles, ketones, tertiary amines, esters of organic acids, dialkyl sulphoxides, sulforane and mixtures thereof.

* * * * *